(12) United States Patent
Spickermann

(10) Patent No.: US 11,872,336 B2
(45) Date of Patent: Jan. 16, 2024

(54) DIALYSIS MACHINE HAVING BLOOD LEAK SENSOR

(71) Applicant: Fresenius Medical Care Deutschland GmbH, Bad Homburg (DE)

(72) Inventor: Reiner Spickermann, Wasserlosen-Burghausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 661 days.

(21) Appl. No.: 17/049,630

(22) PCT Filed: Apr. 17, 2019

(86) PCT No.: PCT/EP2019/059972
§ 371 (c)(1),
(2) Date: Oct. 22, 2020

(87) PCT Pub. No.: WO2019/206773
PCT Pub. Date: Oct. 31, 2019

(65) Prior Publication Data
US 2021/0244867 A1  Aug. 12, 2021

(30) Foreign Application Priority Data
Apr. 23, 2018 (DE) .................. 10 2018 109 702.6

(51) Int. Cl.
*A61M 1/16* (2006.01)
*A61M 1/36* (2006.01)

(52) U.S. Cl.
CPC ........ *A61M 1/1692* (2013.01); *A61M 1/3626* (2013.01); *A61M 2205/15* (2013.01); *A61M 2205/18* (2013.01); *A61M 2205/3306* (2013.01)

(58) Field of Classification Search
None
See application file for complete search history.

(56) References Cited

U.S. PATENT DOCUMENTS

2011/0221889 A1* 9/2011 Knox .................. G08B 17/107
348/135
2012/0194335 A1* 8/2012 Burbank ............. A61M 1/1611
340/522

FOREIGN PATENT DOCUMENTS

DE       19605260       11/1996

* cited by examiner

*Primary Examiner* — Chester T Barry
(74) *Attorney, Agent, or Firm* — Jacobson Holman PLLC

(57) ABSTRACT

The present invention relates to a dialysis machine having a dialyzer, an extracorporeal blood circuit, a dialysis solution circuit, and a control unit, wherein a blood leak sensor is arranged downstream of the dialyzer in the dialysis solution circuit, wherein the control unit is configured to initiate an error routine when the signal of the blood leak sensor shows an indication of a presumed blood leak, and wherein a further sensor is furthermore arranged downstream of the dialyzer in the dialysis solution circuit, wherein the control unit is configured to use the signal of the further sensor correlated in time with the signal of the blood leak sensor as a suppression criterion for the initiation of the error routine.

14 Claims, 1 Drawing Sheet

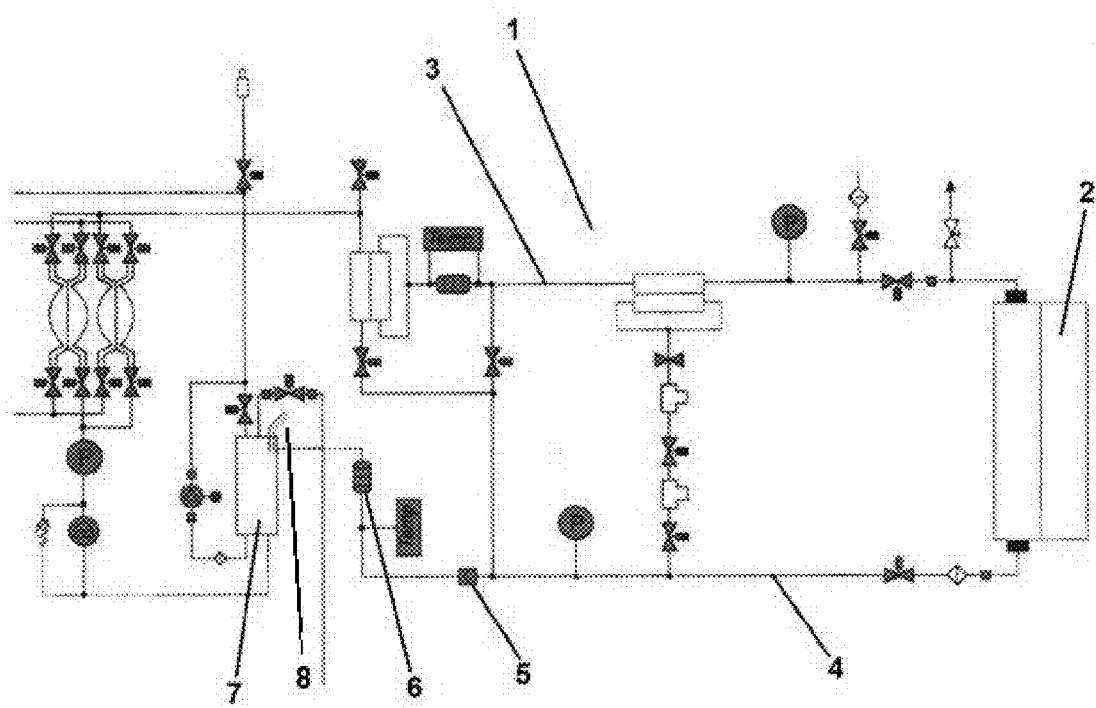

DIALYSIS MACHINE HAVING BLOOD LEAK SENSOR

The invention relates to a dialysis machine having a dialyzer, an extracorporeal blood circuit, a dialysis solution circuit, and a control unit.

As part of a dialysis treatment for renal replacement therapy, blood is conducted in an extracorporeal blood circuit through a dialyzer in which it comes into contact with a dialysis solution via a semipermeable membrane. The membrane has pores that permit a diffusion of small molecules (electrolytes, urea) from the blood into the dialysis solution, but with large molecules such as proteins and blood cells being held back.

An unwanted intake of blood into the dialysis solution can occur in the case of damage in the semipermeable membrane. To be able to recognize such a defect, it is known in the prior art to arrange a sensor downstream of the dialyzer in the dialysis solution circuit with which the presence of blood in the dialysis solution flowing out from the dialyzer can be recognized. Known examples include optical sensors that carry out an extinction measurement. If the sensor signal shows a specific abnormality, the control unit of the machine triggers an alarm and/or effects an immediate pump stop.

It is a disadvantage of existing solutions of this type that false activations can occur due to an intake of air into the dialysis solution (e.g. due to afterdegassing or poor venting of the dialyzer).

It is the object of the invention to provide a concept to reduce the number of such false activations or to at best avoid them overall.

Against this background, the invention relates to a dialysis machine having a dialyzer, an extracorporeal blood circuit, a dialysis solution circuit, and a control unit, wherein a blood leak sensor is arranged downstream of the dialyzer in the dialysis solution circuit, wherein the control unit is configured to initiate an error routine when the signal of the blood leak sensor shows an indication of a presumed blood leak, wherein a further sensor is furthermore arranged downstream of the dialyzer in the dialysis solution circuit, and wherein the control unit is configured to use the signal of the further sensor correlated in time with the signal of the blood leak sensor as a suppression criterion for the initiation of the error routine.

In accordance with the invention, the error routine is therefore at least temporarily suppressed when the signal of the further sensor also shows a specific abnormality in temporal correlation that allows a disruptive factor such a an intake of air to be concluded, for example. The indication of a presumed blood leak or the abnormality can comprise a passing of a threshold value, that is, in the sense of an exceeding of an upper limit or in the sense of a falling below of a lower limit.

BRIEF DESCRIPTION OF THE DRAWINGS

FIG. 1 shows a flow diagram of a portion of the dialysis liquid circuit of a dialysis machine in accordance with the invention.

The arrangement of a blood leak sensor in the dialysis solution circuit and downstream of the dialyzer is known per se. The sensor serves the recognition of intakes of blood into the dialysis solution flowing out of the dialyzer. The invention is therefore based on the idea of making the initiation of an error routine provided for an intake of blood into the dialysis liquid not solely dependent on whether the signal of the blood leak sensor shows an indication of a presumed blood leak, but rather of polling further measurement values that are determined for the dialysis liquid downstream of the dialyzer. The risk of a false activation can thus be reduced.

Provision is made in an embodiment that the further sensor is a sensor that makes use of a measurement process differing from the blood leak sensor and/or detects a measurement parameter differing from the blood leak sensor, with provision preferably being made that the blood leak sensor is configured. It is thus ensured that the signal of the further sensor represents an actual control and does not simply duplicate the same indication.

Provision is made in an embodiment that the further sensor is a sensor whose signal is influenced by air intakes into the dialysis liquid and whose signal is not influenced or is influenced less by blood intakes into the dialysis liquid. Air intakes into the consumed dialysis liquid that are caused, for example, by afterdegassing or by poor venting of the dialyzer represent a possible cause for false positive signals of the blood leak sensor. An effective check can therefore take place using sensor signals that can recognize air intakes and can distinguish them from blood signals, and errors can be avoided.

Provision is made in an embodiment that the further sensor is a conductivity sensor. The arrangement of a conductivity sensor arranged downstream of the dialyzer in the dialysis liquid circuit is known per se, in particular in connection with the measurement of the dialysis dosage (online clearance measurement, OCM). This measurement comprises a time-corrected comparison of the conductivities of the dialysis liquid upstream and downstream of the dialyzer, with it being assumed that the permeability of the membrane for urea is in a fixed ratio to its permeability for electrolytes.

Provision is made in an embodiment that an air separator is arranged downstream of the dialyzer and that the further sensor is an air detector, preferably a level sensor, arranged at the air separator. The arrangement of an air separator downstream of the dialyzer in the dialysis solution circuit is also known per se. It should be avoided by an air separator that the accuracy of the volumetric balancing of the dialysis liquid that is required for determining and regulating the liquid volume taken from the patient is not impaired by air intakes into the dialysis liquid. The air intakes that are to be removed by the air separator arranged downstream of the dialyzer are exactly those air intakes caused, for example, due to afterdegassing or poor venting of the dialyzer, that can also be responsible for false signals at the blood leak sensor.

The signals of the air detector or of the conductivity sensor are, on the one hand, particularly well suited as suppression criteria in the sense of the invention because sensors are used that can already anyway be present in the dialysis liquid circuit for other reasons so that no additional apparatus effort arises. These measurement values are furthermore particularly well suited since air intakes and blood intakes at these sensors cause different reactions. An air intake thus as a rule results in a collapse of the conductivity signal while a blood intake should hardly influence the conductivity of the dialysis liquid due to the nominally identical electrolyte content. The signal of the air detector remains fully uninfluenced by a blood intake while an air intake results in a level displacement at the air separator.

Provision is made in an embodiment that an air separator is arranged downstream of the dialyzer in the dialysis solution circuit and that two further sensors are provided, namely a conductivity sensor and an air detector, preferably a level sensor, arranged at the air separator, with the control unit being configured to use the temporally correlated signals of both of these further sensors as suppression criteria for the initiation of the error routine. A particularly clear reduction of the false activations of the error routine can be achieved by using these two pieces of information.

Provision is made in an embodiment that the temporal correlation is determined using the volume flow of the dialysis liquid and using the internal circuit volumes present between the corresponding sensors. The temporal correlation preferably therefore does not mean a simultaneous observation of the different measurement values, but it is rather taken into account that the dialysis liquid requires a certain time to flow from one sensor to the further sensor. If, for example, an internal circuit volume of vi cm³ is present between a blood leak sensor and a conductivity sensor arranged downstream thereof and if the dialysis liquid flows at a volume flow of f, cm³/s, the routine in accordance with the invention thus uses the conductivity signal at the time t+$t_1$ as the suppression criterion in this embodiment, where t corresponds to the time of the abnormal blood leak signal and $t_1$ corresponds to the correlation time period that results from the quotient $v_1/f_1$.

Provision is made in an embodiment that the control unit is configured only to initiate the error routine after the end of a waiting period during which the abnormality at the blood leak sensor is recognized several times or continuously. Provision can therefore be made that a temporal alarm suppression known per se additionally takes place, with the signal of the blood leak sensor being observed over a specific waiting period of, for example, at least two seconds, at least five seconds, or at least ten seconds, and with the error routine only being initiated when the initially observed abnormality remains or repeats during the observation time period.

Provision is made in an embodiment that the control unit is configured to poll the signal of the further sensor several times or continuously during the waiting period and to use these measurement values as suppression criteria. Provision is made as part of this embodiment that not only the signal of the blood leak sensor is observed over a specific waiting period, but also the signal of the further sensor or sensors. A further reduction of false activations can thus be achieved.

Provision is made in an embodiment that the control unit is configured to extend the waiting period if a signal that allows a disruptive factor to be concluded is recognized at the further sensor. No final suppression of the error routine therefore takes place in this embodiment, but only an extension of the waiting period. This is based on the consideration that an air intake should always only be temporary and should show a relatively abrupt signal behavior while a blood leak results in a more slowly starting or disappearing longer-continuing discoloration of the consumed dialysis liquid. If therefore a blood leak is actually present, a state should be adopted after an extended waiting period in which state the signals of the further sensors remain normal.

Provision is made in an embodiment that the error routine includes the output of an alarm signal. Suitable alarm signals include acoustic or visual alarm signals that can be output directly at the dialysis machine and/or a spatially remote monitoring terminal.

Provision is made in an embodiment that the error routine includes a treatment stop. A treatment stop can comprise the shutting down of a blood pump arranged in the extracorporeal blood circuit and/or of a dialysis liquid pump arranged in the dialysis liquid circuit.

Provision is made in an embodiment that the blood leak sensor is an optical sensor, preferably a sensor for carrying out an extinction measurement. On the use of such sensors, false activations can occur due to air bubbles since both blood intakes and air intakes typically result in a signal attenuation; the latter due to dispersion, refraction, reflection, etc. A use of the concept in accordance with the invention for an alarm suppression is therefore particularly sensible on the use of such sensors.

A unit for carrying out a hemodialysis, a hemodiafiltration, or a hemofiltration is understood as a dialysis machine within the framework of the present invention. The control unit of the machine is connected to said sensors, that is, to the blood leak sensor and to the further sensor or sensors. An algorithm is stored on the control unit that implements the configuration in accordance with the invention of the control unit to initiate and optionally to suppress an error routine.

A dialysis process and a process for monitoring a dialysis treatment in which the signal of the further sensor correlated in time with the signal of the blood leak sensor is used as the suppression criterion for the initiation of the error routine can be implemented using the dialysis machine in accordance with the invention.

Further details and advantages of the invention result from the following embodiment shown with reference to the FIGURE. The only FIGURE shows a flow diagram of a portion of the dialysis liquid circuit of a dialysis machine in accordance with the invention.

The flow diagram shows that region of the dialysis liquid circuit 1 of a machine configured in accordance with the invention that is located close to the dialyzer 2. The further regions of the dialysis liquid circuit 1 are not relevant to the representation of the present invention and were accordingly omitted in the representation. In addition, the following explanation is restricted to the naming and description of those elements of the dialysis liquid circuit 1 which are integral to the understanding of the present invention.

The dialysis liquid circuit 1 comprises a feed line 3 through which dialysis liquid is introduced into the dialyzer 2. In the dialyzer, the dialysis liquid comes into contact with the blood of the patient that is conducted through the dialyzer 2 using an extracorporeal blood circuit, not shown. The contact takes place via a semipermeable membrane having small pores that permit a diffusion of small molecules such as electrolytes and urea between the blood and the dialysis solution, but hold back large molecules such as proteins and blood cells in the blood. The consumed dialysis solution is led off from the dialyzer 2 via the return line 4.

Blood can cross into the dialysis solution due to damage in the semipermeable membrane of the dialyzer, which already has to be avoided due to a contamination of the dialysis liquid circuit. An endangering of the patient, which is naturally not to be tolerated, can furthermore also occur in the case of a high crossover rate. An optical blood leak sensor 5 is therefore located in the return line 4 and determines any blood present in the consumed dialysis solution by an optical extinction measurement. If an indication of a presumed blood leak is recognized, an initiation of an error routine occurs that comprises a visual and an acoustic alarm output and initiates an emergency stop of the treatment, e.g. by stopping the pumps and/or closing the chambers.

The extinction measurement is prone to false activations due to air inclusions, for example, that likewise effect an attenuation of light conducted through the dialysis liquid, inter alia by scattering effects. A temporal trigger suppression was therefore already known in the prior art in which an error routine was only triggered after the end of a specific waiting period in which the abnormality in the signal of the blood leak sensor occurs repeatedly or continuously. However, non-negligible false activations also occur on the use of such a temporal trigger suppression.

The invention makes use of the fact against this background that further sensors are present in the return line 4 whose measurement values are influenced by the presence of air and which are not influenced or are at most slightly influenced by the presence of blood.

The dialysis machine, on the one hand, namely comprises a conductivity sensor 6 arranged in the return line 4. This conductivity sensor 6 generally also participates in the determination of the dialysis dosage as part of an online clearance measurement (OCM) which comprises a time-corrected comparison of the conductivities of the dialysis liquid upstream and downstream of the dialyzer and starts from the assumption that the permeability of the semipermeable membrane located in the dialyzer 2 for urea is in a fixed ratio to its permeability for electrolytes. The signal of the conductivity sensor 6 is at most slightly influenced by blood intakes due to the comparable electrolyte compositions, whereas temporary drops in the conductivity occur with air intakes.

The dialysis machine furthermore comprises an air separator 7 which is arranged in the return line 4 and at which a level sensor 8 is arranged which is shown by two probe pins in the FIGURE. The air separator 7 generally serves to monitor any air intakes into the dialysis liquid so that such possible air intakes can be taken into account in the balancing of the dialysis liquid and the determination of the liquid volume taken from the patient is not falsified. The signal of the level sensor 8 is not influenced at all by any blood intakes, but is influenced by air intakes.

The signal of the conductivity sensor 6 and the signal of the level sensor 8 as suppression criteria on the initiation of the error routine are taken into account within the framework of a variant of the concept in accordance with the invention for preventing false activations. This means that a control query takes place before the initiation of the error routine due to an abnormality in the signal of the blood leak sensor as to how the signals of the conductivity sensor 6 and of the level sensor 8 have changed in temporal correlation.

Temporal correlation here does not mean simultaneity, but a time offset is rather considered that corresponds to the time the dialysis liquid needs with a given flow to flow from the blood leak sensor 5 to the conductivity sensor 6 or to the air separator 7.

If an abnormality is recognized in temporal correlation at the conductivity sensor 6 and at the level sensor which allows a conclusion of an air intake, the error routine is at least temporarily suppressed and the waiting period is extended.

False activations are very effectively avoided using the invention, while the error routine is still reliably triggered on actual blood intakes and the treatment security can thus be ensured to an unchanged extent.

The invention claimed is:

1. A dialysis machine having a dialyzer, an extracorporeal blood circuit, a dialysis solution circuit, and a control unit, wherein a blood leak sensor is arranged downstream of the dialyzer in the dialysis solution circuit; wherein the control unit is configured to initiate an error routine when the signal of the blood leak sensor shows an indication of a presumed blood leak; and wherein a further sensor is furthermore arranged downstream of the dialyzer in the dialysis solution circuit, characterized in that
the control unit is configured to use the signal of the further sensor correlated in time with the signal of the blood leak sensor as a suppression criterion for the initiation of the error routine, wherein the further sensor is arranged downstream of the blood leak sensor and the signals of the blood leak sensor and the further sensor do not reflect simultaneous observations of their respective measured values.

2. A dialysis machine in accordance with claim 1, characterized in that the further sensor is a sensor that makes use of a measurement process differing from the blood leak sensor and/or detects a measurement parameter differing from the blood leak sensor.

3. A dialysis machine in accordance with claim 1, characterized in that the further sensor is a conductivity sensor.

4. A dialysis machine in accordance with claim 1, characterized in that an air separator is arranged downstream of the dialyzer; and in that the further sensor is an air detector arranged at the air separator.

5. A dialysis machine in accordance with claim 1, characterized in that an air separator is arranged downstream of the dialyzer in the dialysis solution circuit; and in that two further sensors are provided, namely a conductivity sensor and an air detector arranged at the air separator, with the control unit being configured to use the temporally correlated signals of both of these further sensors as suppression criteria for the initiation of the error routine.

6. A dialysis machine in accordance with claim 1, characterized in that the control unit is configured to initiate the error routine only after the end of a waiting period during which the abnormality at the blood leak sensor is recognized several times or continuously.

7. A dialysis machine in accordance with claim 6, characterized in that the control unit is configured to poll the signal of the further sensor several times or continuously during the waiting period and to use these measurement values as suppression criteria.

8. A dialysis machine in accordance with claim 6, characterized in that the control unit is configured to extend the waiting period when a signal is recognized at the further sensor that allows a conclusion on a disruptive factor.

9. A dialysis machine in accordance with claim 1, characterized in that the error routine comprises the output of an alarm signal and/or a treatment stop.

10. A dialysis machine in accordance with claim 1, characterized in that the blood leak sensor is an optical sensor.

11. A dialysis machine in accordance with claim 1, characterized in that the further sensor is a sensor that makes use of a measurement process differing from the blood leak sensor and/or detects a measurement parameter differing from the blood leak sensor, with provision being made that the blood leak sensor is configured such that its signal is influenced by air intakes into the dialysis liquid and its signal is not influenced or is influenced less by blood intakes into the dialysis liquid.

12. A dialysis machine in accordance with claim 1, characterized in that an air separator is arranged downstream of the dialyzer; and in that the further sensor is a level sensor arranged at the air separator.

13. A dialysis machine in accordance with claim 1, characterized in that an air separator is arranged downstream of the dialyzer in the dialysis solution circuit; and in that two further sensors are provided, namely a conductivity sensor and a level sensor arranged at the air separator, with the control unit being configured to use the temporally correlated signals of both of these further sensors as suppression criteria for the initiation of the error routine.

14. A dialysis machine in accordance with claim 1, characterized in that the blood leak sensor is an optical sensor for carrying out an extinction measurement.

\* \* \* \* \*